United States Patent
De Oliveira Souza et al.

(10) Patent No.: US 11,492,567 B2
(45) Date of Patent: Nov. 8, 2022

(54) METHOD FOR PRODUCING BIOLUBRICANT FROM VEGETABLE OIL, AND BIOLUBRICANT

(71) Applicants: PETROLEO BRASILEIRO S.A.—PETROBRAS, Rio de Janiero (BR); UNIVERSIDADE FEDERAL DO CEARA—UFC, Fortaleza (BR)

(72) Inventors: Stephanie De Oliveira Souza, Fortaleza (BR); Rosana Maria Alves Saboya, Fortaleza (BR); Jose Andre Cavalcanti Da Silva, Rio de Janeiro (BR); Italo Castro Rios, Fortaleza (BR); Francisco Murilo Tavares De Luna, Fortaleza (BR); Fatima Andrea Lima Girao, Fortaleza (BR); Celio Loureiro Cavalcante, Jr., Fortaleza (BR)

(73) Assignees: PETROLEO BRASILEIRO S.A.—PETROBRAS, Rio de Janiero (BR); UNIVERSIDADE FEDERAL DO CEARA—UFC, Fortaleza (BR)

( * ) Notice: Subject to any disclaimer, the term of this patent is extended or adjusted under 35 U.S.C. 154(b) by 1 day.

(21) Appl. No.: 15/734,644

(22) PCT Filed: Jun. 5, 2019

(86) PCT No.: PCT/BR2019/050205
§ 371 (c)(1),
(2) Date: Dec. 3, 2020

(87) PCT Pub. No.: WO2019/232604
PCT Pub. Date: Dec. 12, 2019

(65) Prior Publication Data
US 2021/0230495 A1    Jul. 29, 2021

(30) Foreign Application Priority Data

Jun. 7, 2018    (BR) ........................ 102018011523-5

(51) Int. Cl.
*C10M 105/42*    (2006.01)
*C07C 67/08*    (2006.01)
(Continued)

(52) U.S. Cl.
CPC ........... *C10M 105/42* (2013.01); *C07C 67/08* (2013.01); *C07C 69/708* (2013.01);
(Continued)

(58) Field of Classification Search
None
See application file for complete search history.

(56) References Cited

U.S. PATENT DOCUMENTS

| | | | | |
|---|---|---|---|---|
| 2009/0285728 A1* | 11/2009 | Miller | ................ | C11C 3/006 422/187 |
| 2011/0282084 A1* | 11/2011 | Potula | ................ | C11C 3/00 554/219 |
| 2017/0211015 A1* | 7/2017 | Kannan | ................ | C11C 3/14 |

FOREIGN PATENT DOCUMENTS

| | | |
|---|---|---|
| BR | PI0105888 A | 8/2003 |
| BR | PI0905200 A2 | 3/2011 |
| BR | 102014019273 A2 | 8/2016 |

OTHER PUBLICATIONS

Lathi, et al., "Green approach for the preparation of biodegradable lubricant base stock from epoxidized vegetable oil," Applied Catalysis B: Environmental, 69: 207-212 (2007).
(Continued)

*Primary Examiner* — Vishal V Vasisth
(74) *Attorney, Agent, or Firm* — J.A. Lindeman & Co., PLLC

(57) ABSTRACT

The present invention describes a process for obtaining a biolubricant from vegetable oil, which comprises the steps
(Continued)

of (a) esterification reaction of the product of vegetable oil hydrolysis using a branched aliphatic alcohol; (b) epoxidation reaction of the esters obtained in step (a); and (c) nucleophilic substitution reaction of the epoxidated esters obtained in step (b) using a branched aliphatic alcohol. The present invention also describes a biolubricant obtained from the process. More specifically, a biolubricant is described that is produced from a ricinoleic fatty acid, whose formula is illustrated in FIG. 1 of the present invention, and where $R_1$ is a hydroxyl or it is from the formula $R_3COO^-$, with $R_3$ being an alkyl radical $C_1$-$C_3$, preferably a methyl radical; and $R_2$ consists of a straight chain of hydrocarbons $C_4$-$C_8$ and a branched chain of hydrocarbons $C_1$-$C_3$.

20 Claims, 1 Drawing Sheet

(51) Int. Cl.
  *C07C 69/708* (2006.01)
  *C10M 105/40* (2006.01)
  *C10M 177/00* (2006.01)
  *C10N 20/02* (2006.01)
  *C10N 30/10* (2006.01)
  *C10N 70/00* (2006.01)

(52) U.S. Cl.
  CPC ........ *C10M 105/40* (2013.01); *C10M 177/00* (2013.01); *C10M 2207/2895* (2013.01); *C10M 2207/301* (2013.01); *C10N 2020/02* (2013.01); *C10N 2030/10* (2013.01); *C10N 2070/00* (2013.01)

(56) References Cited

OTHER PUBLICATIONS

Syahir et al., "A review on bio-based lubricants and their applications," Journal of Cleaner Production, 168: 997-1016 (2017).
Salimon et al., "Chemically modified biolubricant basestocks from epoxidized oleie acid: Improved low temperature properties and oxidative stability," Journal of Saudi Chemical Society, 15: 195-201 (2011).
Campanella et al., "Lubricants from chemically modified vegetable oils," Bioresource Technology, 101: 245-254 (2010).
International Search Report in International Application PCT/BR2019/050205, dated Jul. 30, 2019.

* cited by examiner

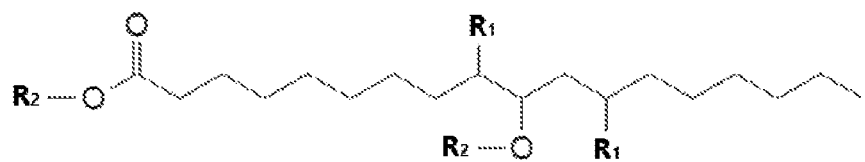

METHOD FOR PRODUCING BIOLUBRICANT FROM VEGETABLE OIL, AND BIOLUBRICANT

This application is a 371 of PCT/BR2019/050205, filed Jun. 5, 2019.

FIELD OF INVENTION

This invention is in relation to a process for obtaining biolubricants by chemically modifying the structure of vegetable oils.

BACKGROUND OF THE INVENTION

Frequent oscillations in the price of oil and the environmental damage caused by fossil-derived products drive the development of products made from new raw materials.

It is within the context of materials other than oil that biolubricants emerge. The term biolubricant is commonly used for lubricants that are biodegradable and non-toxic to the environment and to human beings. They may be obtained from vegetable oils, such as, for example, castor oil, soybean oil, and sunflower oil, among others.

The majority of biolubricants are esters obtained through chemical modification of vegetable oils. Vegetable oils are comprised of triglycerides formed by saturated, monounsaturated, and polyunsaturated compounds.

However, the presence of unsaturation generally means that vegetable oil derivatives are more susceptible to oxidation according to the number of double bonds found in their composition and their configurations.

Thus, although the biolubricants obtained from vegetable oils have the advantage of being biodegradable and the efficiency of lubrication of a raw material, they present limited thermal and oxidative stability.

To solve this problem, chemical modifications to the structure of the vegetable oil are necessary.

The document "Synthesis of new derivatives from vegetable sunflower oil methyl esters via epoxidation and oxirane opening" (pages, X; Alfos, C, 2001) is a study on the synthesis of new products that may be used in the area of lubricants. The raw material used consists of methyl esters from sunflower oil.

In that study, first there is the epoxidation reaction of the oil's methyl esters, and subsequently the opening of the formed oxirane ring. One of the routes described to open the ring was a nucleophilic substitution reaction using a linear alcohol, in which ethanol and octanol were tested.

However, the products obtained present a fluidity temperature that is undesirable for use in biolubricants, ranging between −4° C. and −13° C.

Brazilian patent document PI 0905200-3 uses castor oil as a raw material for biolubricant production. Production occurs from the esterification reaction of the product of vegetable oil hydrolysis, which is in the range of 75-85% ricinoleic acid, with alcohol content from 2 to 8 carbons. The ester obtained then reacts with a carboxylic acid anhydride.

However, the production process described in PI 0905200-3 uses expensive catalysts that have handling risks.

However, it is an objective of this invention to provide a process for obtaining biolubricants that present physical and chemical properties that are desirable for their intended use, employing commercial catalysts that do not present risks for handling or industrial use.

SUMMARY OF THE INVENTION

This invention is in relation to a process for obtaining biolubricants from vegetable oils.

The process includes the steps of (a) esterifying the product from vegetable oil hydrolysis using a branched aliphatic alcohol, (b) epoxidation of the esters in step (a), and (c) nucleophilic substitution of the epoxidated esters obtained in step (b) using a branched aliphatic alcohol.

A second objective of this invention is to provide a biolubricant obtained from the described process.

More specifically, this invention is intended to provide a biolubricant produced from the ricinoleic fatty acid in accordance with the process described. The biolubricant in this invention comprises a mixture of compounds from the formula

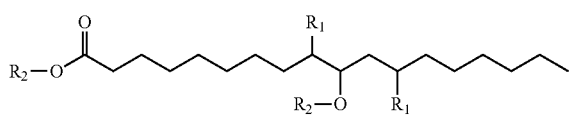

where:
$R_1$ is a hydroxyl or it is from the formula $R_3COO^-$, where $R_3$ is an alkyl radical $C_1$-$C_3$; and $R_2$ consists of a straight chain of hydrocarbons $C_4$-$C_8$ and a branched chain of hydrocarbons $C_1$-$C_3$.

BRIEF DESCRIPTION OF THE FIGURES

FIG. 1 shows the formula of the biolubricant compound, the purpose of this invention, where:
$R_1$ is a hydroxyl or it is from the formula $R_3COO^-$, where $R_3$ is an alkyl radical $C_1$-$C_3$; and $R_2$ consists of a straight chain of hydrocarbons $C_4$-$C_8$ and a branched chain of hydrocarbons $C_1$-$C_3$.

DETAILED DESCRIPTION OF THE INVENTION

This invention is in relation to a process for obtaining a biolubricant from a vegetable oil that comprises the following steps:

(a) esterification reaction of the product of hydrolysis of the vegetable oil using a branched aliphatic alcohol;

(b) epoxidation reaction of the esters obtained in step (a); and (c) nucleophilic substitution reaction of the epoxidated esters obtained in step (b) using a branched aliphatic alcohol.

The process of this invention suggests, first, the use of a branched aliphatic alcohol in any one of steps (a) and/or (c). The alcohol consists of a straight chain of hydrocarbons $C_4$-$C_8$ and a branched chain of hydrocarbons $C_1$-$C_3$. Preferably 2-ethylhexanol alcohol is used in steps (a) and/or (c).

In a preferred method of this invention, the vegetable oil used as the raw material is castor oil and the product of its hydrolysis is mainly ricinoleic fatty acid. Within the context of the invention, "mainly" is understood to mean the presence of more than 85% ricinoleic acid in the product of hydrolysis.

In order to obtain better yields and a purer product, the product of vegetable oil hydrolysis undergoes a purification process to remove by-products, which occurs prior to the esterification reaction in step (a).

Steps (a) and (c) of the process described here are performed using low-cost, commercially available acid catalysts. Preferably a polystyrene-based ion exchange sulfonic resin is used, commercially known as Amberlyst-15, as a catalyst in step (a), and p-Toluenesulfonic acid is used in catalysis of the nucleophilic substitution reaction of step (c).

The catalysts used in this invention allow conversions greater than 90%, attaining conversions of up to 99%, thus facilitating the steps of separation and subsequent treatment of the products obtained.

The esterification reaction in step (a) of the product of hydrolysis may be performed within a temperature range between 80 and 100° C., over 4 to 8 hours. A mass ratio of catalyst/vegetable oil varying between 2.5 to 7.5% is used, and a molar ratio of fatty acid(s)/alcohol that varies between 1:2 and 1:4 is used.

In a method of implementing this invention, the process described includes, after step (a), one or more of the following additional steps:

($a_1$) cooling of the product obtained in step (a) to ambient temperature;

($a_2$) filtration of the cooled product for removal of the catalyst; and ($a_3$) distillation of the filtered product to remove the excess alcohol.

The epoxidation reaction in step (b) may be performed using formic acid and hydrogen peroxide, in a temperature range of 20 to 40° C., for a period of 8 to 24 hours. A molar ratio of ester/formic acid/hydrogen peroxide varying between 1:1:2 and 1:2:6 is used.

In a method of implementing this invention, the process described comprises, after step (b), one or more of the following additional steps:

($b_1$) separation of phases by decantation of the product obtained in step (b);

($b_2$) neutralization of the organic phase with a salt and subsequent washing; and ($b_3$) distillation of the neutralized and washed product to remove the excess formic acid and unreacted hydrogen peroxide.

The nucleophilic substitution reaction in step (c), in turn, consists of opening the oxirane ring formed in the epoxidation reaction, which may be performed in a temperature range between 80 and 100° C., over a period of 2 to 6 hours. Preferably a mass ratio of catalyst/vegetable oil varying between 5 to 15% is used, and a molar ratio of fatty acid(s)/alcohol varying between 1:2 and 1:4 is used.

In a method of implementation, after step (c) the process comprises one or more of the following additional steps:

($c_1$) separation of phases by decantation of the product obtained in step (c);

($c_2$) neutralization of the organic phase with a salt and subsequent washing; and ($c_3$) distillation of the neutralized and washed product to remove the excess alcohol.

Preferably a solution of sodium bicarbonate is used in the step to neutralize the organic phase and distilled water for washing in steps ($b_2$) and ($c_2$).

Following is a diagram of the reactions that occur in steps (a), (b) and (c) of this process, using ricinoleic acid as the product of vegetable oil hydrolysis, and 2-ethylhexanol as the alcohol in steps (a) and (c).

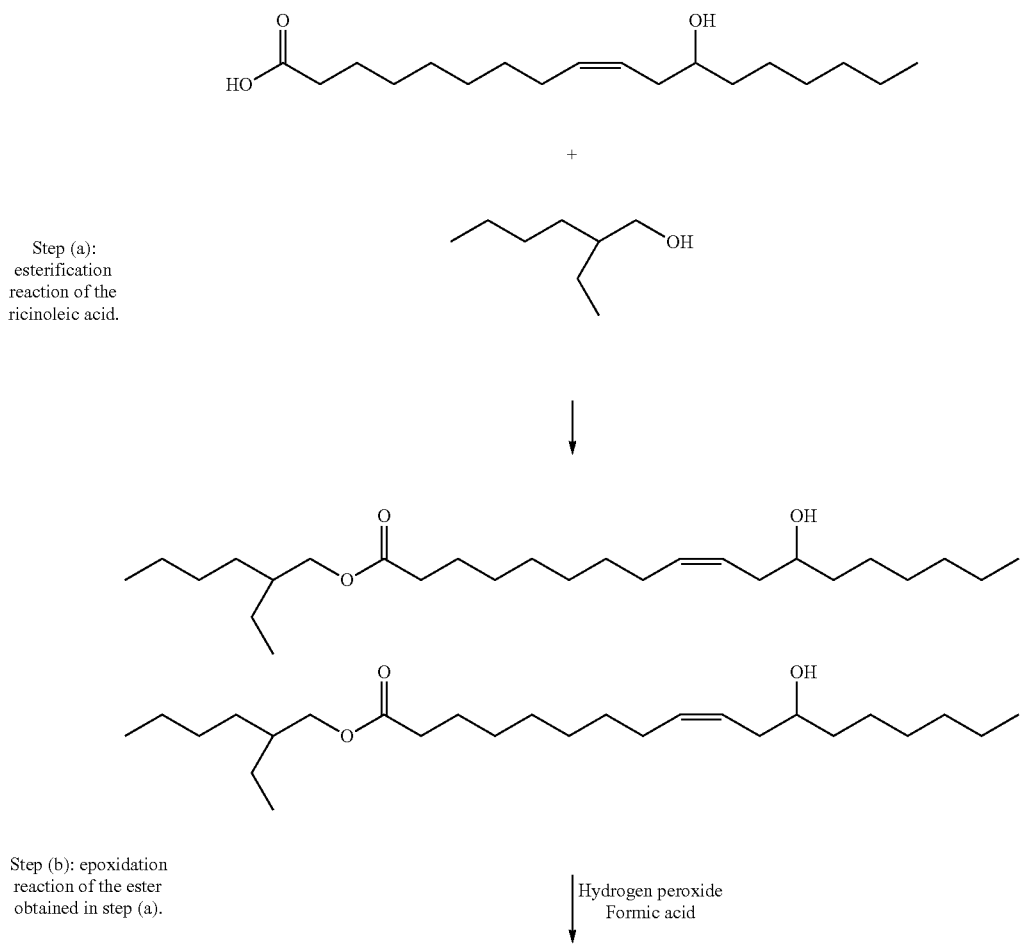

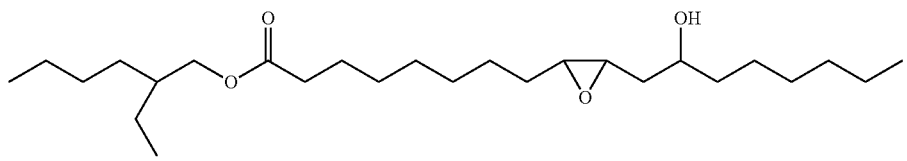

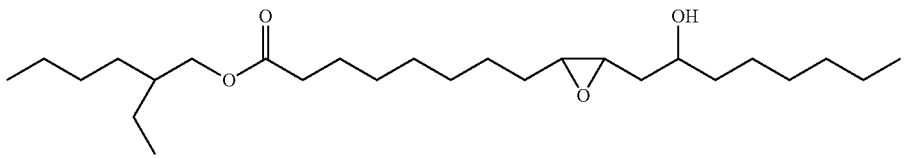

Step (c): nucleophilic substitution reaction of the epoxidated ester obtained in step (b).

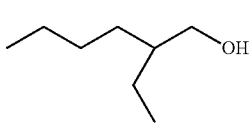

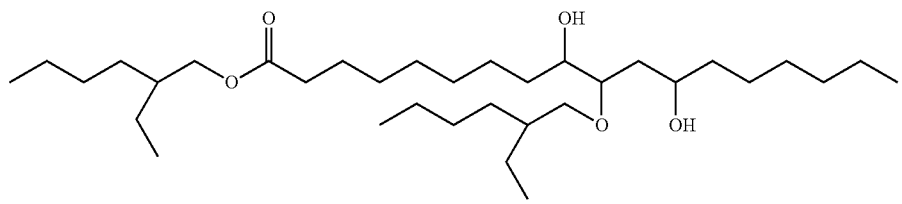

The biolubricants obtained through the process of this invention present desirable physical and chemical properties for this type of application.

For example, the products present low fluidity temperature (preferably in the range of −40° C. to −45° C.), high oxidative stability (preferably in the range of 30 to 55 minutes), high viscosity rate (preferably above 120), and low total acidity value. In addition, the biolubricants from this invention also present high biodegradability, with a maximum half-life of 28 days.

In a method of implementation of this invention, the process described here comprises a subsequent step (d), referring to the conversion reaction of the hydroxyls present in the structure of the product obtained in step (c) with a carboxylic acid anhydride.

Step (d) is preferably performed using potassium hydroxide as the catalyst. Among the preferred carboxylic acid anhydrides are acetic, propanoic and butanoic anhydride.

Step (d) occurs in a temperature range between 80 and 100° C., for a period of 10 to 14 hours, using a mass ratio of catalyst/ester varying between 1 to 5%, and a molar ratio of ester/acetic anhydride varying between 1:1 and 1:2.

In a method of implementation, after step (d) the process described comprises one or more of the following additional steps:

($d_1$) dilution in an organic solvent of the product obtained in step (d);

($d_2$) adjustment of the pH between 5 and 6 and subsequent washing;

($d_3$) drying of the product obtained in ($d_2$)

($d_4$) distillation of the product after drying for removal of the excess anhydride.

Preferably hexane is used as the dilution solvent in step ($d_1$), while the pH adjustment and washing are performed using a sodium chloride solution in step ($d_2$). Drying in step ($d_3$) is preferably done using sodium sulfate.

In step (d), the hydroxyl radicals present in the structure of the product formed in step (c) are converted into alkyl-carboxyl radicals. That conversion further improves the thermal and oxidative stabilities of the formed biolubricant, in addition to lowering the fluidity temperature to values below −45° C. Thus the range of application of the products obtained is expanded.

Below is a diagram of the reaction in step (d) using acetic anhydride in the conversion reaction.

Step (d): conversion reaction of the hydroxyls present in the structure of the product formed in step (c).

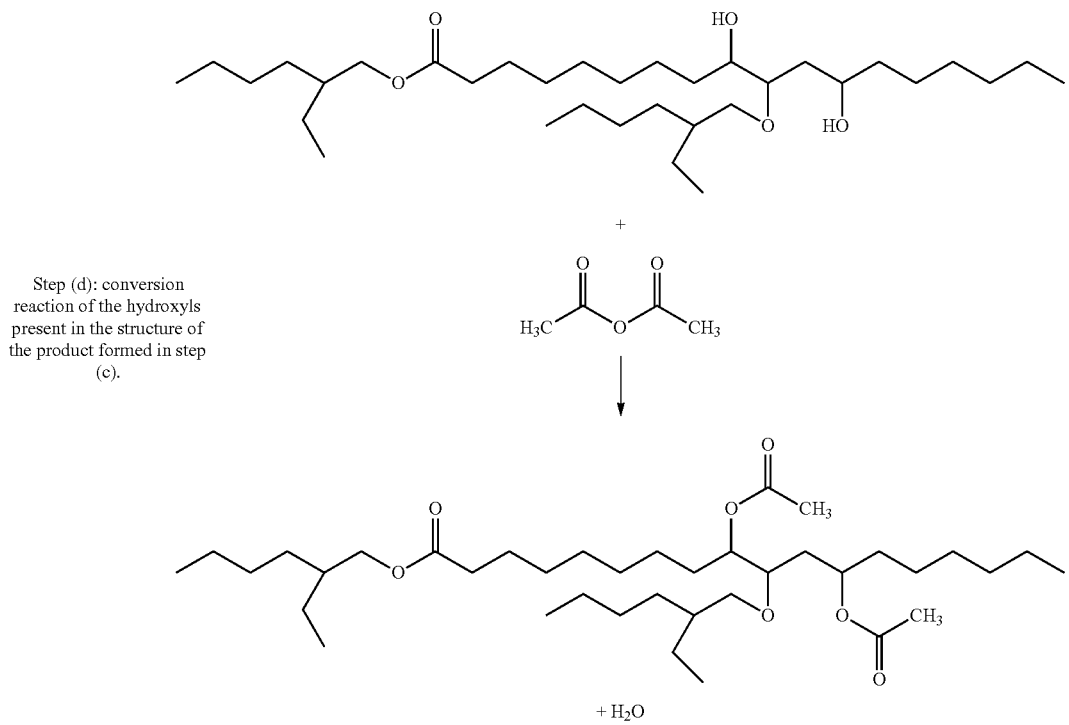

In addition, this invention is also in reference to the biolubricant produced from the product of hydrolysis of a vegetable oil in accordance with the process described.

More specifically, the biolubricant is produced from the ricinoleic fatty acid in accordance with the process of this invention. The biolubricant comprises a mixture of compounds from the following formula:

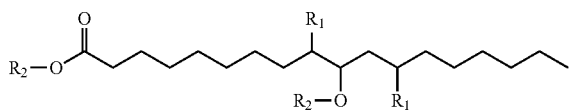

where:

$R_1$ is a hydroxyl or it is from the formula $R_3COO^-$, where $R_3$ is an alkyl radical $C_1$-$C_3$; and $R_2$ consists of a straight chain of hydrocarbons $C_4$-$C_8$ and a branched chain of hydrocarbons $C_1$-$C_3$. Preferably, $R_3$ is a methyl radical.

In the method of this invention, $R_1$ is a hydroxyl when step (d) is absent in the process of obtaining the biolubricant, that is, when there is no conversion of the hydroxyls present in the structure of the product obtained in step (c) of the process described here.

The biolubricant in this invention presents physical and chemical properties that are advantageous for this type of application, such as: a viscosity index (VI) greater than 120, preferably between 120 and 150, fluidity temperature lower than −40° C., preferably between −40° C. and −50° C., and oxidative stability between 30 and 60 minutes.

The following description will begin with preferred implementations of the invention. As will be evident to any technician in the matter, the invention is not limited to these specific implementations.

EXAMPLES

Example 1—Step (a)

The reaction from step (a) was attained using fatty acids obtained in the hydrolysis of castor oil. The alcohol 2-ethylhexanol was used in the esterification reaction.

To do this, the sample of fatty acids was weighed (60 g) and then transferred to a 500-mL container. From the weighed mass of the initial material, the volume of alcohol was calculated (130 mL) for each molar ratio and the mass of the catalyst used (3 g of Amberlyst-15).

The stoichiometric ratio between fatty acids and alcohol was calculated and the mass of the catalyst was obtained in relation to the ricinoleic fatty acid.

The reaction apparatus also had a reflux system to promote condensation of the volatile compounds and a hot plate, which was kept at a temperature of 80 to 100° C. for a reaction time of 4 to 8 hours. The system was agitated within a range of 800 to 1200 rpm.

The system was kept under an inert atmosphere of $N_2$ to prevent oxidation of the materials. At the end of the reaction the product was cooled until it reached ambient temperature, then it was passed through a vacuum filter to remove the catalyst of the reaction medium.

Next the formed ester was distilled using a Kugelrohr apparatus to remove the excess alcohol, where the samples remained for 40 to 80 minutes at a temperature of 70 to 90° C.

The conversions obtained using gas chromatography were 90 to 95%, and the mass yield was higher than 90%.

Example 1—Step (b)

The esters obtained from the reaction in step (a) were epoxidated. The epoxidation was achieved using performic acid generated in situ.

To initiate the reaction, 70 g of the esters (ricinoleate) were weighed and then transferred to a 500-mL container. The system was agitated within a range of 800 to 1200 rpm.

Next, formic acid was added to the reaction medium (6 mL), and then hydrogen peroxide was added (46 mL).

The reaction was monitored for 8 to 24 h at a temperature of 20 to 40° C. The reaction mixture was transferred to a separation funnel. After separation of the phases, the organic phase (upper portion), was then neutralized with a solution of sodium bicarbonate 5%, and washed with distilled water.

To remove the formic acid and hydrogen peroxide still present, the product was distilled using the Kugelrohr apparatus at 40 to 80° C. for 40 to 80 minutes.

The conversions obtained from proton nuclear magnetic resonance were 95 to 99%, and mass yield was higher than 95%.

Example 1—Step (c)

First a sample of epoxidated ricinoleate was weighed (60 g), then it was transferred to a container that was connected in a reflux system and agitated constantly between 800 to 1200 rpm.

During the process, the system was kept pressurized with an inert atmosphere of $N_2$. The volume of 2-ethylhexanol alcohol (67 mL) was measured, then the alcohol was transferred to a 500-mL recipient that contained the catalyst p-Toluenesulfonic acid (6 g) until total dissolution.

The mixture was slowly added to the reaction medium. The reaction was monitored for 2 to 6 hours, and after the end of the reaction, the reaction mixture was transferred to a separation funnel.

After separation of the phases, the organic phase (upper portion) was then neutralized with a solution of 300 mL of sodium bicarbonate 5%, and washed with 150 mL of distilled water.

To remove the excess alcohol, the product was distilled using a Kugelrohr apparatus at a temperature of between 80 and 100° C. for 40 to 80 minutes.

The conversions obtained from proton nuclear magnetic resonance were 95 to 99%, and mass yield was higher than 90%.

Example 1—Step (d)

Acetic anhydride was used in the step of converting the hydroxyls present in the structure of the product obtained in step (c).

After the oxirane ring was opened, the ricinoleate was weighed (60 g) and mixed with acetic anhydride (20 mL) in a 500-mL container that was agitated constantly at ambient temperature and inert atmosphere.

After the ester was completely mixed with acetic anhydride, the catalyst potassium hydroxide (KOH) (1 g) was added. The mixture was kept at a temperature between 80-100° C. for 12 hours, and agitated constantly. After this step, the process of purifying the products was initiated.

The purification process consisted of dilution in hexane, washing with an aqueous solution saturated with sodium chloride (NaCl) containing 5% in sodium bicarbonate mass ($NaHCO_3$) until the pH was adjusted to between 5 and 6, washed with an aqueous solution saturated with NaCl, and dried with sodium sulfate ($Na_2SO_4$).

After the washing steps, the product was distilled using a Kugelrohr apparatus at a temperature between 110 and 125° C. for 30 minutes.

Conversions of 90 to 99% were obtained in gas chromatography with a flame ionization detector (Varian CP3800), an apolar DB-5 column in which the carrier gas used was argon, and the injected sample volume was 1 μL.

Comparative Example 1

Tests were done comparing the effect of different alcohols in step (c) of the process described in this invention, in order to demonstrate the superior efficiency of the branched 2-ethylhexanol alcohol, in comparison with other linear and cyclical alcohols.

The results of the physical and chemical properties of the products after the reactions from opening the oxirane ring with different alcohols are shown in table 1.

TABLE 1

Comparison of physical and chemical properties obtained using different alcohols used in step (c)

| | | Opening reagents | | | | |
|---|---|---|---|---|---|---|
| Properties | Methods | Ethanol AM1 | Hexanol AM2 | Cyclohexanol AM3 | Octanol AM4 | 2-ethylhexanol AM5 |
| Specific mass at 20° C. (g/cm³) | ASTM D1298 | 0.906 | 0.907 | 0.908 | 0.906 | 0.907 |
| Viscosity @ 40° C. (cSt) | ASTM D445 | 29.125 | 31.764 | 30.132 | 30.982 | 32.905 |
| Viscosity @ 100° C. (cSt) | | 5.32 | 5.928 | 5.940 | 5.900 | 6.046 |
| Viscosity index | ASTM D2270 | 117 | 134 | 145 | 138 | 132 |
| Fluidity temperature (° C.) | ASTM D97 | −12.0 | −9.0 | −9.0 | −6.0 | −42.0 |
| Oxidative stability (min) | ASTM D2272 | 16.1 | 25.6 | 30.5 | 40.9 | 50.1 |

As shown in Table 1, the product that presented the best physical and chemical properties was that which used the branched alcohol (2-ethyl-hexanol) in the nucleophilic substitution reaction.

The fluidity temperature and oxidative stability obtained with this branched alcohol are highlighted as having been highly superior to those obtained with the other alcohols.

The description that has been provided up to this point regarding the purpose of this invention should only be considered as one possible implementation or implementations, and any specific characteristics provided herein must be understood only as something that was written to facilitate comprehension. Therefore, they cannot in any way be considered as limiting on the invention, which is limited to the scope of the following claims.

The invention claimed is:

1. A process for obtaining a biolubricant from vegetable oil, wherein it comprises the following steps:
   (a) esterification reaction of the product of hydrolysis of the vegetable oil using a branched aliphatic alcohol;
   (b) epoxidation reaction of the esters obtained in step (a); and
   (c) nucleophilic substitution reaction of the epoxidated esters obtained in step (b) using a branched aliphatic alcohol, wherein the branched aliphatic alcohol is 2-ethyl-hexanol.

2. The process of claim 1, wherein the branched aliphatic alcohol used in step (a) consists of a straight chain of hydrocarbons $C_4$-$C_8$ and a branched chain of hydrocarbons $C_1$-$C_3$.

3. The process of claim 2, wherein the branched aliphatic alcohol used in step (a) is 2-ethyl-hexanol.

4. The process of claim 1, wherein said vegetable oil is castor oil and the product of its hydrolysis is ricinoleic fatty acid.

5. The process of claim 1, wherein said product of vegetable oil hydrolysis undergoes a purification process prior to the esterification reaction in step (a).

6. The process of claim 1, wherein said step (a) is using a polystyrene-based ion exchange sulfonic resin as the catalyst in a temperature range between 80 and 100° C., for a period of 4 to 8 hours, in which a catalyst/vegetable oil mass ratio is used that varies between 2.5 and 7.5%, and a fatty acid(s)/alcohol molar ratio is used, which varies between 1:2 and 1:4.

7. The process of claim 1, wherein it comprises, subsequent to step (a), one or more of the following additional steps:
($a_1$) cooling of the product obtained in step (a) to ambient temperature;
($a_2$) filtration of the cooled product for removal of the catalyst; and
($a_3$) distillation of the filtered product to remove the excess alcohol.

8. The process of claim 1, wherein said step (b) is using formic acid and hydrogen peroxide, in a temperature range of 20 to 40° C., for a period of 8 to 24 hours, in which a molar ratio of ester/formic acid/hydrogen peroxide varying between 1:1:2 and 1:2:6 is used.

9. The process of claim 1, wherein it comprises, subsequent to step (b), one or more of the following additional steps:
($b_1$) separation of phases by decantation of the product obtained in step (b);
($b_2$) neutralization of the organic phase with a salt and subsequent washing; and
($b_3$) distillation of the neutralized and washed product to remove the excess formic acid and unreacted hydrogen peroxide.

10. The process of claim 1, wherein said step (c) is using p-Toluenesulfonic acid as the catalyst, in a temperature range between 80 and 100° C., for a period of 2 to 6 hours, in which a catalyst/vegetable oil mass ratio varying between 5 and 15% is used, and a fatty acid(s)/alcohol molar ratio varying between 1:2 and 1:4 is used.

11. The process of claim 1, wherein it comprises, subsequent to step (c), the following additional steps:
($c_1$) separation of phases by decantation of the product obtained in step (c);
($c_2$) neutralization of the organic phase with a salt and subsequent washing; and
($c_3$) distillation of the neutralized and washed product to remove the excess alcohol.

12. The process of claim 1, wherein it comprises a step (d) of reaction of the reaction product obtained in step (c) with carboxylic acid anhydride.

13. The process of claim 12, wherein said step (d) is performed using potassium hydroxide as the catalyst and a carboxylic acid anhydride selected from among acetic, propanoic and butanoic anhydride, in a temperate range of between 80 and 100° C., for a period of 10 to 14 hours, in which a mass ratio of catalyst/ester varying between 1 to 5% is used, and a molar ratio of ester/acetic anhydride varying between 1:1 and 1:2 is used.

14. The process of claim 12, wherein it comprises, subsequent to step (d), one or more of the following additional steps:
($d_1$) dilution in an organic solvent of the product obtained in step (d);
($d_2$) adjustment of the pH between 5 and 6 and subsequent washing;
($d_3$) drying of the product obtained in ($d_2$); and
($d_4$) distillation of the product after drying to remove the excess anhydride.

15. A biolubricant produced from the product of vegetable oil hydrolysis, wherein it is obtained from the process of claim 1.

16. The biolubricant of claim 15, wherein said product of hydrolysis is a ricinoleic fatty acid, in which the biolubricant comprises a mixture of compounds from the formula $$R_2-O-\underset{O}{\overset{\parallel}{C}}-(CH_2)_7-\underset{R_2-O}{\overset{R_1}{C}H}-CH_2-\underset{R_1}{C}H-(CH_2)_5-CH_3$$

where:
$R_1$ is a hydroxyl or $R_3COO^-$, where $R_3$ is an alkyl radical $C_1$-$C_3$; and $R_2$ consists of a straight chain of hydrocarbons $C_4$-$C_8$ and a branched chain of hydrocarbons $C_1$-$C_3$.

17. The biolubricant of claim 16, wherein $R_1$ is a hydroxyl when step (d) is absent in the process of obtaining the biolubricant.

18. The biolubricant of claim 16, wherein the biolubricant presents a viscosity index (IV) higher than 120, a fluidity temperature lower than −40° C., and an oxidative stability between 30 to 60 minutes.

19. The biolubricant of claim 16, wherein $R_3$ is a methyl radical.

20. The biolubricant of claim 18, wherein the biolubricant presents a viscosity index (IV) between 120 to 150, and a fluidity temperature between −40° C. to −50° C.

* * * * *